United States Patent
Salter (10) Patent No.: US 10,926,605 B2
(45) Date of Patent: Feb. 23, 2021

(54) WEARABLE MONITOR FOR PERSONAL THERMAL CONTROL IN A VEHICLE

(71) Applicant: JAGUAR LAND ROVER LIMITED, Coventry (GB)

(72) Inventor: Spencer Salter, Coventry (GB)

(73) Assignee: JAGUAR LAND ROVER LIMITED, Coventry (GB)

( * ) Notice: Subject to any disclaimer, the term of this patent is extended or adjusted under 35 U.S.C. 154(b) by 0 days.

(21) Appl. No.: 16/171,122

(22) Filed: Oct. 25, 2018

(65) Prior Publication Data

US 2019/0126721 A1 May 2, 2019

(30) Foreign Application Priority Data

Oct. 27, 2017 (GB) ...................................... 1717664

(51) Int. Cl.
| | | |
|---|---|---|
| *B60H 1/00* | (2006.01) | |
| *A61B 5/00* | (2006.01) | |
| *A61B 5/01* | (2006.01) | |
| *A61B 5/0205* | (2006.01) | |

(52) U.S. Cl.
CPC ....... *B60H 1/00742* (2013.01); *A61B 5/0008* (2013.01); *A61B 5/01* (2013.01); *A61B 5/681* (2013.01); *A61B 5/02055* (2013.01); *A61B 5/6824* (2013.01); *A61B 2560/0242* (2013.01); *A61B 2562/0271* (2013.01)

(58) Field of Classification Search
CPC .......................... B60H 1/00742; A61B 5/0008
See application file for complete search history.

(56) References Cited

U.S. PATENT DOCUMENTS

| | | | |
|---|---|---|---|
| 2014/0094707 A1 | 4/2014 | Farrington et al. | |
| 2016/0016454 A1 | 1/2016 | Yang et al. | |
| 2016/0252407 A1* | 9/2016 | Ikeda ................... | G01K 13/002 |
| | | | 374/29 |
| 2018/0050235 A1* | 2/2018 | Tan ..................... | A61B 5/02416 |
| 2018/0266834 A1* | 9/2018 | Cronin ................. | B60R 16/037 |
| 2018/0326814 A1* | 11/2018 | Prakah-Asante ........................... | |
| | | | B60H 1/00742 |

FOREIGN PATENT DOCUMENTS

| | | |
|---|---|---|
| EP | 3187846 A1 | 7/2017 |
| WO | 2011109716 A2 | 9/2011 |
| WO | 2015157670 A1 | 10/2015 |
| WO | 2017031129 A2 | 2/2017 |
| WO | 2017065797 A1 | 4/2017 |

OTHER PUBLICATIONS

Search and Examination Report, GB1717664.5, dated Apr. 25, 2018, 10 pages.

* cited by examiner

*Primary Examiner* — Anne Marie Antonucci
*Assistant Examiner* — Abdalla A Khaled
(74) *Attorney, Agent, or Firm* — Miller Nash Graham & Dunn LLP (57) ABSTRACT

A wearable electronic device can include a communication unit configured to communicate with external devices, a heat flow sensor configured to measure a rate of heat energy flowing through a user's skin, and a processor configured to calculate a target ambient temperature for the user based on the measured heat flow through the user's skin.

7 Claims, 4 Drawing Sheets

WEARABLE MONITOR FOR PERSONAL THERMAL CONTROL IN A VEHICLE

CROSS REFERENCE TO RELATED APPLICATION

This application claims priority to and the benefit of GB 1717664.5 filed Oct. 27, 2017, which is incorporated herein by reference in its entirety.

TECHNICAL FIELD

The present disclosure relates to a wearable device. Particularly, but not exclusively, the disclosure relates to wearable device comprising a heat flow sensor which optionally can be used to control a temperate regulating device. Aspects of the invention relate to the device and methods of use of the device.

BACKGROUND

There is a desire to improve the comfort of persons travelling in a vehicle.

There are several factors that affect a vehicle occupant's comfort, including the environmental conditions within the vehicle. Whilst vehicle occupants may have some control over the environmental conditions (for example road vehicles often provide user controls for adjusting heating and cooling of the interior of the vehicle), the inputs provided by the occupants can sometimes be sub-optimal. For example some occupants might overcompensate for a difference in the actual temperature and the desired temperature, which can be inefficient.

Furthermore, it is known that humans are unable to accurately determine their body temperature, typically as they are unable to accurately compensate for environmental factors (such as environmental temperature, wind, solar loading etc.) nor for factors which may cause the body temperature to increase (such as physical exercise). This inaccuracy also leads to sub-optimal inputs for environmental control systems.

Another factor that affects the comfort of a vehicle occupant is whether they are experiencing motion sickness. Motion sickness (which is also referred to as kinetosis) is a condition that can affect persons travelling in a vehicle and includes car sickness and seasickness. Motion sickness can be induced by motion of the vehicle, wherein the vehicle occupant's vestibular system senses the motion, but the vehicle occupant's visual system provides an output that is in conflict with the sensed motion. For example, a passenger in a road vehicle looking at a location within the vehicle (for example reading a book) may perceive very little motion visually, because the location (e.g. the book) is only moving a small amount relative to the user. However the vehicle itself may be moving a greater amount, thus the passenger's vestibular system senses a greater movement. As a result, the passenger may begin to feel the symptoms of motion sickness. The symptoms of motion sickness include nausea, dizziness and fatigue, and if the symptoms are not alleviated in time, motion sickness can result in vomiting.

The onset of motion sickness depends on several factors, including the direction and frequency of the motion—in the case of a road vehicle, this motion may be determined by the surface roughness of the road, the radius of a corner being traversed, etc. The unique physiological response of the vehicle occupant also affects the onset of motion sickness, with certain people being more susceptible to motion sickness than others. The age and gender of the vehicle occupant can also have an effect on the onset of motion sickness.

Whilst the physiological effect of motion sickness may differ between persons, motion sickness can be quantified by a motion sickness dose value (MSDV), which is defined in standard ISO 2631 and BS6841 1987. A motion sickness dose value is calculated based on a frequency weighted acceleration of a person in a vertical direction and the amount of time the person is experiencing the motion, and gives an indication of the likelihood that the person is experiencing motion sickness.

In order to alleviate the symptoms of motion sickness, it is known to stop the motion of the vehicle where possible. For example, otherwise unnecessary stops can be made during a journey in a road vehicle to attempt to alleviate the symptoms of motion sickness. However such action is inconvenient, and is not always possible (for example during a journey by sea or air, or a road journey on roads where stopping is not permitted or otherwise not possible). Moreover, simply stopping the motion of the vehicle when a person begins to feel the effects of motion sickness may have only limited effectiveness, since the vehicle occupant may only begin feeling the symptoms of motion sickness at a time after the onset of the motion sickness—the earlier that remedial action is taken after the onset of motion sickness, the more effective the remedial action is.

With the advent of autonomous vehicles, the propensity for motion sickness to occur is predicted to increase. Motion sickness in vehicles is known to affect passengers to a greater extent than persons controlling the vehicle. Moreover the usage of road vehicles has the potential to change as vehicle autonomy becomes more prevalent, with vehicle occupants predicted to spend more time engaging with vehicle entertainment systems, performing work related tasks, using personal computing devices, reading etc., increasing the chance for discrepancies between visual input and vestibular response to arise.

Accordingly there is a desire to improve the comfort of vehicle occupants, in particular by reducing the likelihood that the vehicle occupant experiences the symptoms of motion sickness.

SUMMARY

Aspects of the invention relate to a wearable electronic device, and a method, a controller and a system for controlling a vehicle climate system of a vehicle. Aspects and embodiments of the invention provide a wearable device, which optionally integrates with a climate control unit to provide an optimal air output setting and a method of controlling a climate control unit.

In an aspect of the invention there is provided a wearable electronic device comprising: a communication unit configured to communicate with external devices; a heat flow sensor configured to measure a rate of heat energy flowing through a user's skin. As the device comprises a heat flow sensor a more accurate measurement of the user's physiological properties may be made.

In a further aspect of the invention the is provided A wearable electronic device comprising: a communication unit configured to communicate with external devices; a heat flow sensor configured to measure a rate of heat energy flowing through a user's skin; a processor configured to calculate a target ambient temperature for the user in dependence on the measured heat flow through the user's skin; wherein the communication unit is configured to transmit a signal to a vehicle climate system, the signal indicative of the calculated target temperature, wherein the signal is configured to cause the vehicle climate system to provide the target ambient temperature; wherein: the memory is configured to store a plurality of measured values of heat flow through the user's skin over time; and the processor is configured to: determine, in dependence on the plurality of measured values of heat flow through the user's skin over time, a baseline heat flow value; and calculate the target ambient temperature for the user in dependence on the determined baseline heat flow value.

Optionally, the heat flow sensor is a heat flux sensor and wherein the heat flow sensor is a Peltier or Seebeck device. Such sensors are preferred as they provide a direct measure heat flow through a user's skin (for example, the heat flow between the skin of the user and the surrounding environment, such as the heat flow from the skin of the user to the ambient environment and vice versa).

In a further embodiment the device comprises a processor configured to calculate a target ambient temperature for the user in dependence on the measured heat flow through the user's skin; wherein the communication unit is configured to transmit a signal to an external heating or cooling apparatus, the signal indicative of the calculated target temperature, wherein the signal is configured to cause the heating or cooling apparatus to provide the target ambient temperature. Thus the device can be used to control a heating or cooling apparatus, such a climate control unit to ensure end user comfort.

In a further embodiment the device comprises a memory; wherein: the memory is configured to store a plurality of measured values of heat flow through the user's skin over time; and the processor is configured to: determine, in dependence on the plurality of measured values of heat flow through the user's skin over time, a baseline heat flow value; and calculate the target ambient temperature for the user in dependence on the determined baseline heat flow value. The ambient temperature is the temperature of the environment in which the user is located, for example the cabin temperature of a vehicle, and the user's target ambient temperature is an ambient temperature that would improve or optimise the comfort of the user (for example a higher temperature than a current ambient temperature if the user is cold). In a further embodiment the processor is configured to: determine, in dependence on the plurality of measured values of heat flow, a deviation in heat flow through the user's skin from the baseline heat flow value; and calculate the target ambient temperature for the user in dependence on the determined deviation in heat flow through the user's skin from the baseline heat flow value. Optionally, wherein: the memory is configured to store calendar data; and the processor is configured to: determine, in dependence on the calendar data, a first time period during which the heat flow through the user's skin is expected to deviate from the baseline heat flow value; and calculate one or more of: a first target ambient temperature for the user for the first time period; and a second target ambient temperature for the user for a second time period subsequent to the first time period. Using historic values allows for an improved determination of an optimal target temperature to be made. Furthermore the use of calendar data may provide an indication that the occupant will have an increased or elevated, body temperature (for example having been to the gym) and such data is used to further refine the target ambient temperature.

In a further example the device comprises one or more further sensors selected from: a temperature sensor; a heart rate sensor; and a heart rate variability sensor; wherein the processor is configured to calculate the target ambient temperature for the user in dependence on the measured heat flow through the user's skin and one or more further measurements taken by the one or more further sensors. In a further example the communications unit is configured to transmit the signal to a vehicular climate control system.

In another aspect of the invention, there is provided a method for operating a vehicle climate system, the vehicle climate system having a climate control unit configured to control the temperature of one or more regions of a vehicle cabin; the method comprising: receiving, from one or more sensors, data indicative of one or more measured thermal properties of a vehicle occupant (for example a temperature of the vehicle occupant, or a heat flow through the occupant's skin); determining an adapted output for the climate control unit in dependence on the one or more measured thermal properties of the vehicle occupant; instructing the climate control unit to provide the adapted output. Thus dependent on the temperature of the occupant the output of the climate control unit is varied in order to ensure optimal comfort for the occupant.

In a further embodiment, the method further comprises determining a probability of motion sickness for the vehicle occupant in dependence on the one or more measured thermal properties; and determining the adapted output in dependence on the determined probability of motion sickness. When an occupant experiences motion sickness a variation in the climate control unit can help mitigate and reduce the feeling of motion sickness thereby improving comfort.

In a further embodiment, the method comprises determining the probability of motion sickness in dependence if the vehicle occupant is asleep.

In a further embodiment the method further comprising receiving data indicative of a temperature of one or more portions of the occupant using a thermal camera. Optionally, wherein the data comprises image data from the thermal camera, and the method comprises: identifying a region of interest in the image data; determining a temperature of the region of interest in dependence on the image data; and determining the adapted output in dependence on the signal in dependence on the temperature of the region of interest. By using a thermal camera a further measurement of the occupant's thermal properties, such as temperature and rate of heat flow can be made.

In a further embodiment data comprises zone occupancy data from a zone occupancy sensor, and the method comprises: determining, a zone of the vehicle occupied by the vehicle occupant in dependence on the zone occupancy data; and instructing the climate control unit to provide the adapted output to the determined zone. Thus only the zones of the vehicle which are occupied have the adapted output.

In a further embodiment the method comprises retrieving historical data collected by the one or more sensors; determining the climate control unit output in dependence on the historical occupant data and the one or more measured thermal properties. The historic data is used to provide an improved output.

In a further aspect of the invention, there is provided a controller for operating a vehicle climate system, the vehicle climate system having a climate control unit configured to control the temperature of one or more regions of a vehicle cabin; wherein the controller is configured to: receive, from at least one wearable electronic device, one or more sensors, data indicative of one or more measured thermal properties of a vehicle occupant; determine an adapted output for the climate control unit in dependence on the one or more measured thermal properties of the vehicle occupant; instruct the climate control unit to provide the adapted output.

In a still further aspect of the invention, there is provided a system comprising: a controller for operating a vehicle climate system, the vehicle climate system having a climate control unit configured to control the temperature of one or more regions of a vehicle cabin; wherein the controller is configured to: receive, from one or more sensors, data indicative of one or more measured thermal properties of a vehicle occupant; determine an adapted output for the climate control unit in dependence on the one or more measured thermal properties of the vehicle occupant; instruct the climate control unit to provide the adapted output; wherein the climate control unit is configured to provide the adapted output in dependence of the instructions from the controller; the system further comprising the climate control unit and the one or more sensors.

In a yet further aspect of the invention, there is provided a vehicle comprising a controller for operating a vehicle climate system, the vehicle climate system having a climate control unit configured to control the temperature of one or more regions of a vehicle cabin; wherein the controller is configured to: receive, from one or more sensors, data indicative of one or more measured thermal properties of a vehicle occupant; determine an adapted output for the climate control unit in dependence on the one or more measured thermal properties of the vehicle occupant; instruct the climate control unit to provide the adapted output; the vehicle optionally further comprising the climate control unit and the one or more sensors.

BRIEF DESCRIPTION OF THE DRAWINGS

One or more embodiments of the invention will now be described, by way of example only, with reference to the accompanying drawings, in which.

DETAILED DESCRIPTION OF THE EMBODIMENTS

Aspects of the present invention relate to a wearable electronic device, and a method, a system, a controller and a vehicle.

In an example, there is provided a wearable device configured to determine, and collect data relating to a number of physiological properties of the wearer including the rate of heat flow between a wearer of the device and their external environment. There is also provided a system which utilises the data collected by the device to regulate a climate control unit, such as those found in vehicles.

Figure 1:
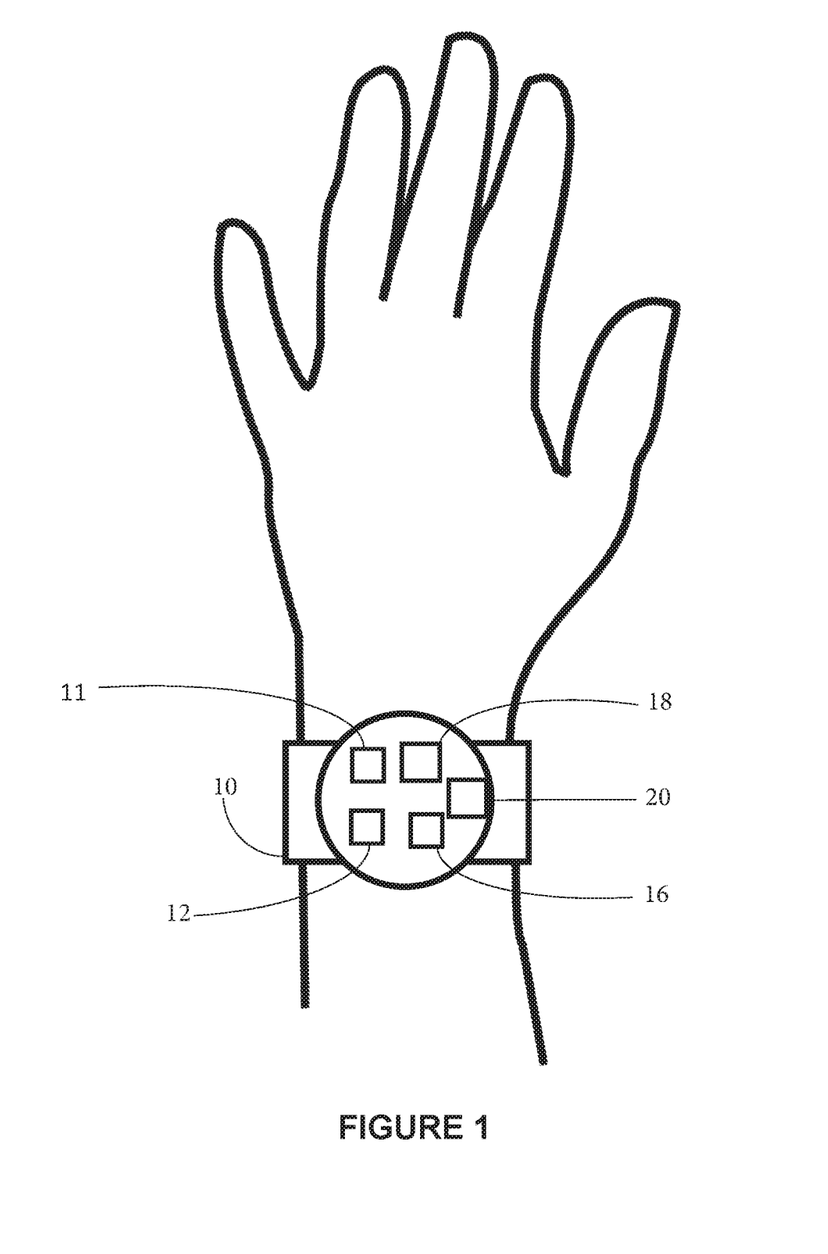
FIG. 1 is a schematic of a wearable device in accordance with some embodiments of the present invention.

FIG. 1 shows a schematic of a wearable device 10. The wearable device 10 is in the form of known wearable devices such as a smart watch, activity tracker, fitness tracker or other portable electronic device that can be worn by a user. Such wearable devices may be attached or carried on the person, via strap or integrated into existing items such as glasses (spectacles), or clothing.

The wearable device described with reference to FIG. 1 is in the form of smart watch/fitness tracker device which is intended to be worn on a wrist of a user. The functionality described for the device is, in further embodiments, incorporated into other types of wearable devices.

The wearable device 10 comprises a first user sensor 12, and one or more further sensors 14, a processor 16 a communication module or transceiver 18 and a memory 20. For the ease of understanding the following description is made with reference to a device comprising four sensors though the number of sensors in the device in further embodiments varies according to the requirements of the device.

The first sensor 12 is a heat flow sensor configured to measure the rate of heat flow from the user to the environment through the skin of the user. The heat flow sensor in an embodiment is a heat flux sensor, or a Peltier or Seebeck device configured to provide a direct measure of heat flow. Preferably the first sensor 12 is positioned within the device 10 such that it is in direct contact with the user's skin so as to provide a direct measure of the heat flow through the skin of a user (that is to say, the heat flow between the skin of the user and the surrounding environment, for example the heat flow from the skin of the user to the ambient environment and vice versa). The heat flow through the skin of the user can be bidirectional. For example, when the user has a higher temperature than the surrounding environment, resultant heat flow may be from the user, through their skin, to the surrounding environment. Similarly, when the temperature of the surrounding environment has a high temperature than the user, resultant heat flow may be from the surrounding environment to the user (though the skin of the user). The heat flow through the user's skin provides a measure of vasodilation/vasoconstriction, temperature of the skin, the humidity, thermal conductivity of the skin passing through the device to the environment in which the user is situated. Such measures are also an indication of the comfort of the user with high levels of heat transfer being indicative of a stressful situation. Such data can therefore provide a direct measure of a user's physiological response and thus provide an indication of the effect of motion sickness on the user.

Advantageously the use of such a heat flow sensor in a wearable device allows the heat flow through the occupant's skin to be accurately measured, which is used to provide a more accurate determination of a likelihood that the occupant is experiencing motion sickness. As the heat flow inherently accounts for other factors such as relative humidity at the skin and other environmental factors it provides an improved measure of the user's temperature regulation than measuring skin temperature alone. In an embodiment the heat flow sensor 12 is Peltier or Seebeck device which provides a direct measure of heat flow and the amount of heat energy flowing through the skin from and to the external environment.

Peltier and Seebeck devices use the thermometric effect and is the direct conversion of temperature differences to electric voltage. A thermometric device creates voltage when there is a different temperature on each side and as such they provide a direct measure, via the voltage of the heat differences and flow. In further embodiments a dual thermo-couple and hydrometer for Rh (Relative humidity) may be used. However the use of the Peltier device is preferred as it provides the same measurements but with a single device. In further embodiments non-contact infrared sensors are also used to determine heat flow.

In addition to the first heat flow sensor 12 the device optionally comprises one or more further sensors 14 configured to measure of parameters which are used in the calculation of user comfort, in particular for the purpose of determining a user's likelihood of experiencing motion sickness. For ease of understanding only one further sensor 14 is shown though in further embodiments a plurality of further sensors are present.

In one example the wearable device further comprises a dynamic motion sensor 14 configured to measure one or more properties of motion (for via an accelerometer or pedometer etc.)—the dynamic motion sensor 14 is configured to measure motion of the wearable device. In further embodiments the further sensors can measure further physiological properties of the user for example, heat rate, skin temperature etc.

The wearable device 10 comprises a processor 16 configured to control the wearable device 10. The processor 16 is configured to control the wearable device in a known manner and furthermore is configured to capture and process the data from the first sensor 12 and the one or more further sensors 14.

The wearable device 10 also comprises a communications module 18 configured to transmit and receive data. The communications module may be a wireless communications transceiver (e.g. Wi-Fi, Bluetooth, etc.) module as known in the art.

In another embodiment, the wearable device 10 is configured to communicate with a further electronic device (not shown), such as a portable device (e.g. a mobile telephone) or a device integrated into a vehicle, the further device comprising a processor configured to process the data from the sensors of the wearable device 10.

In further embodiments, the wearable device 10 can integrate with a fitness tracking, or wellbeing, app in order to provide the user with an indication of their level of activity and lifestyle. Such an app allows a user to log exercise, diet, medication etc. as well as providing a record of the user's heat flow and temperature over the course of time. Such integration is known in the art.

In further embodiments the memory 20 stores historic heat flow and other sensor data.

As such the wearable device 10, with the heat flow sensor 12, can directly measure the user's temperature regulation and automatically compensate, for environmental factors thus providing a more accurate measure of the user's temperature regulation than by solely measuring the skin temperature. As described in further detail below such information may be used to control an environmental unit and furthermore be used to estimate the likelihood of a user experiencing motion sickness.

As the wearable device 10 provides an improved measure of users' physiological properties, in particular via the heat flow through a user's skin, the data is used to control a heating or cooling apparatus to provide a user with an optimal temperature to enhance occupant comfort. In particular, but not exclusively, such heating and cooling apparatus are those found in vehicle as a heating, ventilation and air condition unit (HVAC) or climate control unit.

Figure 2:
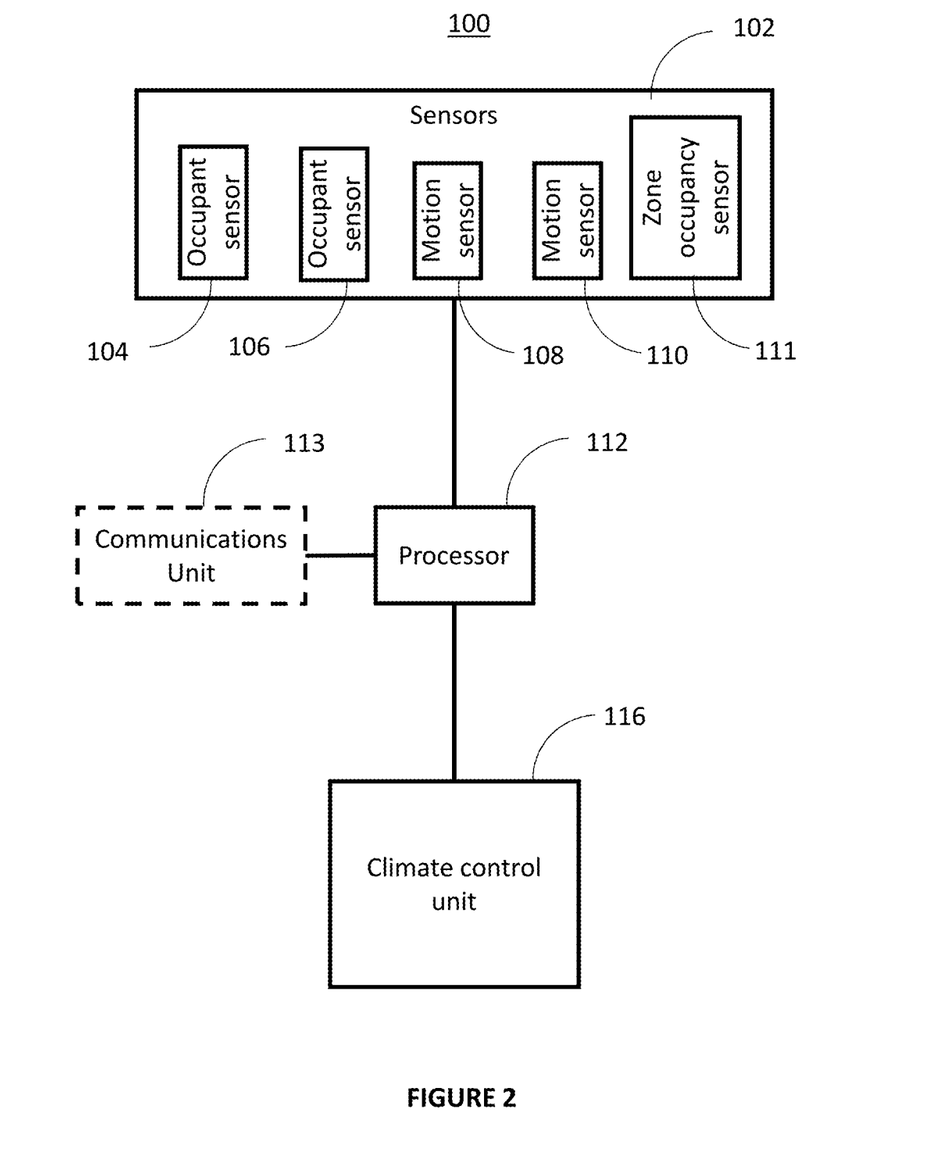
FIG. 2 is a schematic of a system for improving comfort of a vehicle occupant in a vehicle in accordance with an embodiment of the invention.
Figure 3:
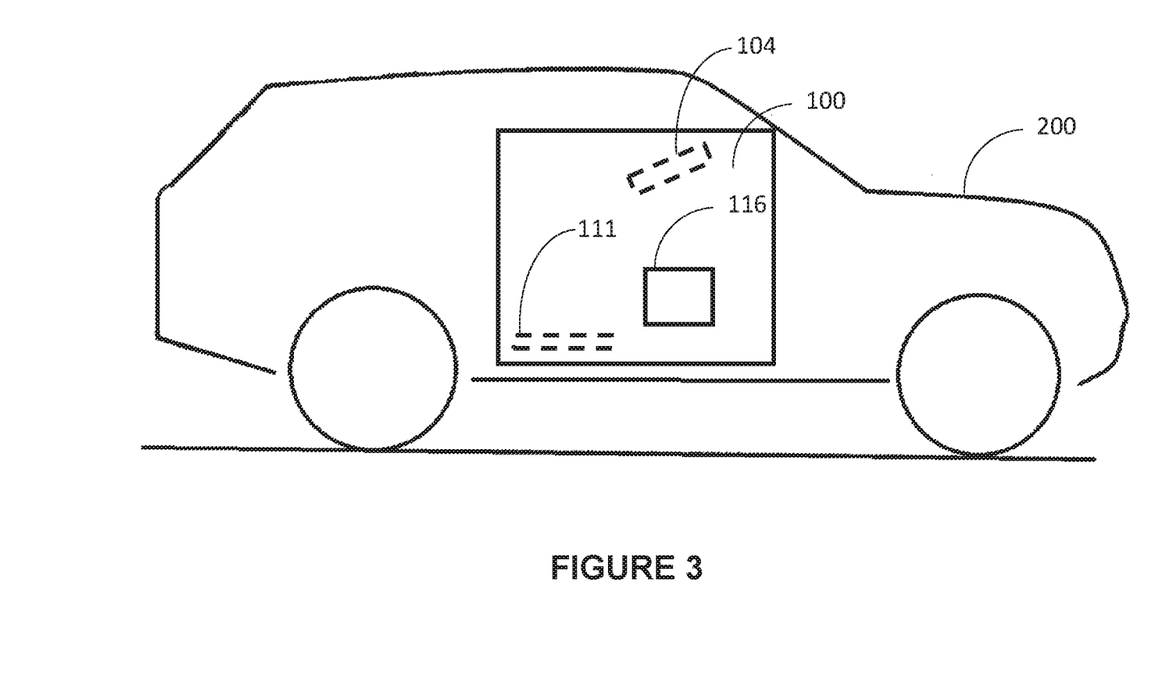
FIG. 3 is a schematic of a vehicle In accordance with an aspect of the invention.

FIG. 2 is a schematic of a system 100 for improving comfort of a vehicle occupant in a vehicle. FIG. 3 shows a vehicle 200 comprising the system 100. As shown in FIG. 3, the vehicle 200 is a car, however it will be appreciated that the present invention may be applied to a wide range of vehicles, including road vehicles, aircraft, boats, etc.

The system 100 comprises a set of sensors 102. The set of sensors 102 includes at least one of: one or more occupant sensors 104, 106 configured to measure physiological properties of an occupant in a vehicle; and one or more vehicle motion sensors 108, 110 configured to measure dynamic motion properties of the vehicle 200. The vehicle motion sensors 108, 110 are any appropriate sensors for measuring the dynamic motion properties of the vehicle 200, for example inertial or other motion-related properties, such as velocity, pitch, yaw, roll etc. In a preferred embodiment, the set of sensors 102 comprises both occupant sensors 104, 106 and vehicle motion sensors 108, 110. The system 100 also comprises a processor 112 in communication with the set of sensors 102. The processor 112 may be connected to the set of sensors 102 by wired or wireless means as is known in the art. In some examples some of the sensors 104, 106, 108, 110 are connected to the processor wirelessly, whilst other sensors 104, 106, 108, 110 are connected by wired means. This is advantageous when some of the sensors 104, 106, 108, 110 are integral to a vehicle whereas other sensors 104, 106, 108, 110 are integrated in an electronic device associated with a vehicle occupant (see below). Optionally the system 100 comprises a communications unit 113, configured to allow wireless communication between the processor 112 and one or more of the sensors 104, 106, 108, 110.

The vehicle motion sensors 108, 110 measure dynamic properties of the vehicle, such as inertial properties, of the vehicle 200 in which the system is implemented. For example, the vehicle motion sensors 108, 110 measure dynamic properties such as one or more of roll angle and/or rate, pitch angle and/or rate, yaw angle and/or rate, acceleration, deceleration, etc. of a vehicle. In one example, the vehicle motion sensors 108, 110 are an inertial measurement unit (IMU) integrated in the vehicle 200 as is known in the art and are commercially available. Advantageously, data collected by the vehicle motion sensors 108, 110 can be used to determine the dynamic motions that the vehicle occupant has been cumulatively subjected to whilst travelling in the vehicle. From this, it is possible to calculate a motion sickness dose value (MSDV) for the occupant using the formula defined in ISO 2631 and BS6841 1987 (or by another suitable method), or other measure of the probability, or likelihood, that the occupant is likely to be experiencing motion sickness. In one example, data from an IMU is used to determine the motion experienced at a particular location within the vehicle corresponding to the position of the occupant, and the MSDV for the occupant at that position can be determined.

The occupant sensors 104, 106 measure one or more physiological properties of an occupant in the vehicle 200, for example the occupant's heart rate, heart rate variability, vasodilation, and skin temperature, skin heat flow. Preferably the occupant sensors 104, 106 comprise at least one of:

- A heart rate sensor configured to measure the heart rate and heart rate variability of the occupant. Increased heart rate, and in particular increased heart rate variability has been found to be an indicator that an occupant is experiencing motion sickness. Thus beneficially this data can be used in a calculation to determine the probability that the occupant is experiencing motion sickness. The heart rate sensor may be any such sensor known in the art.
- A temperature sensor (such as an infrared sensor, thermal camera, thermocouple or other thermoelectric device etc.) configured to measure the temperature of the occupant's skin. It has been found that increased vasodilation is an indication that motion sickness is being experienced by a person. Vasodilation can cause an increase in skin temperature, thus skin temperature can be used in a calculation to determine the probability that the occupant is experiencing motion sickness.

A humidity sensor configured to measure the humidity at the occupant's skin. It has been found that increased perspiration is an indication that motion sickness is being experienced by a person. By measuring humidity at the occupant's skin, the occupant's perspiration can be inferred, and used to calculate a probability that the occupant is experiencing motion sickness.

A heat flow sensor (such as a heat flux sensor, Seebeck, or Peltier device, see below) configured to measure the flow of heat through the occupant's skin. Measuring the flow of heat through the occupant's skin has been found to provide a more accurate indication of vasodilation than just measuring temperature and humidity, since it automatically accounts for changes in temperature that are due to environmental conditions rather than motion sickness. Thus the measured heat flow measured through the occupant's skin can be used in a calculation to determine the probability that the occupant is experiencing motion sickness.

An optical camera configured to record images of the occupant. Motion sickness has been found to cause changes in skin colour, for example due to vasodilation, or due to decreased blood flow to the skin preceding vomiting. Accordingly images of the occupant can be analysed to detect changes in skin colour, which can be used in a calculation to determine the probability that the occupant is experiencing motion sickness. The images may also be used to estimate or determine the age and/or gender of the occupant—it has been found that age and gender affects how likely a person is to experience motion sickness for a given set of conditions. The image data can also be used to determine the amount of time an occupant spends looking up or down. It is known that when an occupant looks downwards the probability of them experiencing motion sickness increases.

In an example the vehicle motion sensors 108, 110 can supplement, or replace, the data from the one or more further sensors 14 of the wearable device 10.

In further examples the sensors determine which zones of the vehicle are occupied. Such data is typically collected in cars, for example via a zone occupancy sensor 111 such as a seat and/or seatbelt sensor.

The set of sensors 102 optionally comprises sensors configured to take environmental measurements, for example:

A temperature sensor (such as an infrared sensor, thermal camera, thermocouple, thermoelectric device etc.) configured to measure the ambient temperature in the vehicle 200. It has been found that ambient temperature can affect the probability that a person will experience motion sickness for a given set of motion conditions.

A temperature sensor (such as an infrared sensor, thermal camera, thermocouple, thermoelectric device etc.) ambient temperature outside the vehicle 200.

A humidity sensor configured to measure the ambient humidity in the vehicle 200. It has been found that ambient humidity can affect the probability that a person will experience motion sickness for a given set of motion conditions.

A sun load sensor (for example a photovoltaic sensor) configured to detect a part of the interior of the vehicle being subjected to a high thermal load due to solar radiation, and thus locally heating that part of the interior of the vehicle.

In one embodiment, one or more of the sensors 104, 106, 108, 110 are associated with a portable electronic device. For example the occupant sensors 104, 106 are included in a portable electronic device or are attached to a portable electronic device, such as a smartphone or tablet. In another example, the occupant sensors 104, 106 are included in a wearable device being worn by the occupant.

Returning to FIG. 2, each sensor 104, 106, 108, 110 is configured to send data to the processor 112. The processor 112 is configured to assess whether the occupant is uncomfortable based on the output of the sensors 104, 106, 108, 110. For example, the processor 112 determines whether the occupant is too hot, too cold, or in conditions that are too humid, based on the data from the occupant sensors 104, 106.

In some embodiments, the processor 112 is also configured to calculate a likelihood that the vehicle occupant is experiencing motion sickness based on data received from the set of sensors. In the case that the system comprises the wearable device 10 of FIG. 3, the processor 112 may either be the wearable device's own processor 16 or a separate processor (for example a processor integrated into the vehicle, wherein the data is transmitted from the wearable device communications module 18 to the vehicle integrated processor via optional communications unit 113). Optionally, the processor 112 is further configured to determine whether an occupant is asleep based on data from the sensors 104, 106, 108, 110 for example by analysing image data from a camera to determine that the occupant has their eyes shut, or by determining that the occupant's heart rate, heart rate variability and/or vasodilation corresponds to the occupant being asleep. Optionally the processor is further configured to determine the age and/or gender of the occupant, for example based on an analysis of image data from a camera, or by retrieving stored data describing the age and/or gender of the occupant.

In one embodiment, the processor 112 is configured to receive historical occupant sensor data describing historical physiological parameters of the occupant. For example, the processor may receive a baseline describing physiological parameters considered to be normal for the occupant, or calculate such a base line based on historical data. In this embodiment, the processor 112 is configured to calculate a likelihood of motion sickness value for the occupant by comparing current data from the sensors to the historical data, to determine if the current physiological parameters of the occupant differ from the historical physiological parameters in a manner indicative of the occupant experiencing discomfort or motion sickness. For example the processor may determine from current data from the occupant sensors 104, 106 that the physiological parameters of the occupant deviate from the baseline in a way that is indicative of discomfort or motion sickness. In this embodiment, the system 100 preferably includes the wearable device 10, which uses the one or more user sensors 12 to collect data describing the physiological parameters of the occupant over time. Advantageously, by using a wearable device for this purpose, data can be collected even after the occupant leaves the vehicle 200, which in turn leads to a more accurate calculation of a baseline.

In a further example of the above embodiment, the processor 112 is also configured to retrieve or otherwise receive user data, such as calendar data, related to the occupant. The user data may be stored on the wearable device 10. The user data is used by the processor to determine a time period during which the physiological parameters of the occupant are expected to deviate from the baseline, due to factors other than the occupant being an uncomfortable temperature, being an uncomfortable humidity, experiencing motion sickness, etc.

Figure 4:
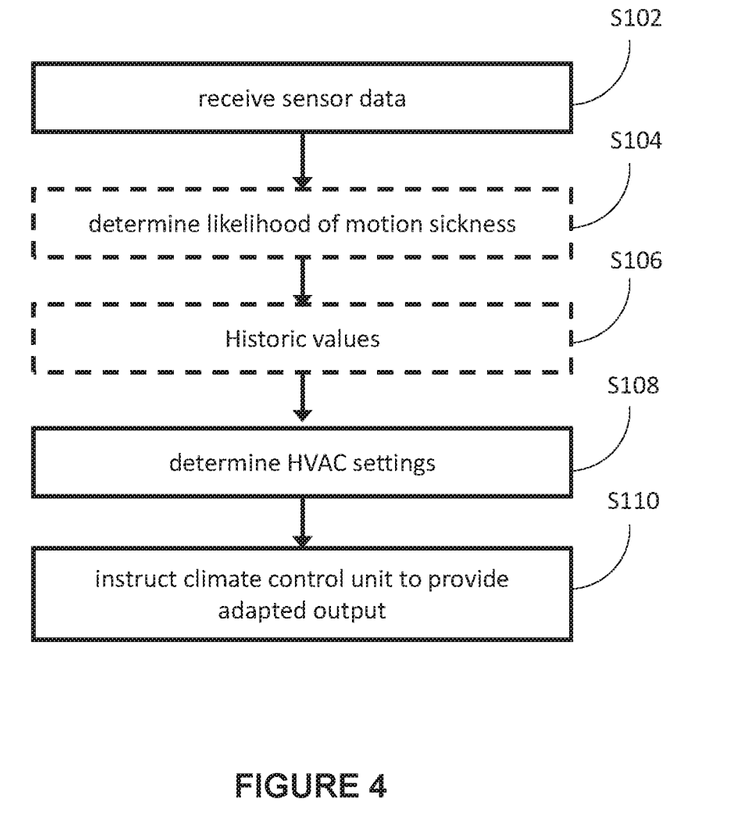
FIG. 4 is a flow diagram of a method for improving comfort of an occupant of a vehicle in accordance with the claimed invention.

FIG. 4 is a flow chart of the process of how the data collected from the wearable device 10, and first sensor 12, is used to control the system for increasing user comfort 100. As described with reference to FIG. 1 the first sensor 12 is a heat flow sensor configured to measure the heat flow through a user's skin.

The following process is described with reference to a single occupant for ease of understanding. In further embodiments the same principles are applied to multiple occupants of the vehicle. In particular it is known for some heating, ventilation, and air conditioning (HVAC) units in vehicles to provide different temperature settings for different parts of the vehicle and the process described below allows for the temperature for one or more of the occupants to be adjusted to an optimal level. In particular data from one or more zone occupancy sensors 111 is used to determine the zone(s) (e.g. the seat) which are presently occupied and adjust the output to of the climate control system, or HVAC unit, to the zones which are occupied.

At step S102 the sensor data including data from the heat flow sensor 12 is received at the processor 112. As described with reference to FIG. 1 the heat flow sensor 12 provides a direct measure of the amount of heating or cooling that a user is currently experiencing which furthermore compensates for environmental factors i.e. the local temperature and humidity.

In further embodiments, in addition to, or in replacement of the heat flow sensor 12 data, data from a thermal camera is used to provide a measure of the occupant temperature. Such image data can be used to identify a region of interest (typically associated with an occupant) and determine a temperature of the region. Such data, as described in detail below with reference to steps S104 to S110 is used to determine a target ambient temperature for the region and occupant.

Optionally the system, at step S104, using the data received in step S102, the processor 112 determines a probability of motion sickness value in step S104. A known symptom of motion sickness is a change in the body's response where the person will attempt to cool down via so-called cold sweats. Such a change is measured as a change in the heat flow through the skin as the amount of heat flow increases as the body attempts to cool down. Such changes in heat flow are typically very rapid and readily identified.

Therefore it is possible to use the data received at step S102 to determine the probability that a wearer of the wearable device is experiencing motion sickness. The probability of motion sickness value is preferably based on the physiological properties of the occupant (from which it can be determined whether they are exhibiting signs of motion sickness, as discussed above) and the motion that the vehicle occupant is subjected to (for example by calculating an MSDV for the occupant). The likelihood, or probability, of motion sickness value can be determined based on the physiological properties and motion in any appropriate manner. In an embodiment, the probability of motion sickness is determined as a weighted sum of the determined motion (or acceleration) experienced by the occupant, for example as calculated as the MSDV, and the physiological (e.g. occupant heart rate, temperature, etc.) and environmental data (e.g. cabin temperature, humidity etc.). In further embodiments this weighted by the percentage time the occupant has spent looking down. In further embodiments any other suitable form of calculation may be used.

Alternatively, or in addition to, data from the occupant sensors 104, 106, 108, 110, such as a camera, is configured to determine the position and orientation of the occupant's head. A factor known to alleviate the feeling of motion sickness experienced by an individual is being able to view the horizon. By viewing the horizon, the user is provided with a visual reference point which can help resolve any conflict between the motion sensed by the vestibular system and the viewed motion. Accordingly, when a user is looking downwards (for example when reading, or utilising a mobile phone, tablet computer or other such device) the amount of horizon that they are able to view is reduced. As such the likelihood of motion sickness for a given user will vary according to their head position, with the likelihood of motion sickness increasing depending on the orientation of their head, which affects the amount of horizon the user can view.

Optionally, at step S106 historic values of the user's heat flow are determined. Step S106 can occur after step S102 (i.e. the step of calculating the probability of motion sickness has been skipped) or after, or before, step S104. If both steps S104 and S106 are performed the order in which the steps are performed may change.

Whilst the heat flow sensor 12 provides an accurate value of the current heat flow experienced by a user there may be underlying reasons for the increase in heat flow which may need to be accounted for. For example, if a user has been exercising then the level of heat flow experienced by a user would typically be much higher as the user would need to cool down after exercise. Such changes in heat flow would typically occur over a sustained period of time and identifiable via historic sensor data. Furthermore, in the embodiments where the wearable device 10 further comprises a calendar, fitness or wellbeing app, instances of physical exercise are readily identified.

In further embodiments a predetermined baseline, based on historic data is used.

At step S106 a baseline of the user's heat flow through the skin can be determined allowing for the ready identification of sudden increases (or decreases) in heat flow.

At step S108 based on the received data as per step S102 and optionally the calculated probability of motion sickness (S104) and historic data (S106), an optimal air output setting, for example an HVAC setting, is determined. In an example, determining an HVAC setting includes defining a target ambient temperature as well as an air flow rate. In an example, air flow is provided by one or more air vents arranged to direct air blown by a fan towards a user. The optimal air output is therefore dependent on the physiological parameters experienced by the user (in particular the heat flow) at a given moment in time. Thus the temperature is actively adjusted to ensure optimal user comfort. In further examples the output is not just air output and also includes any means for changing the temperature such as radiative/conductive heaters, opening the windows, etc.

For example, in the event that it is determined that the user is experiencing a higher rate of heat flow and they are showing a high probability of motion sickness, the HVAC setting may be varied to increase the flow of air in order to provide a distracting stimulus to the user, which is known to alleviate the feeling of motion sickness. In another example where the heat flow through the user's skin is low, and the user is known to have been exercising, and therefore has an elevate body temperature, the temperature setting is adjusted to reduce the ambient air temperature for the user.

In embodiments where the user utilises a lifestyle app to record one or more of exercise, diet, medication etc., this information is also used to determine the temperature setting. For example some medications are known to affect the level of vasoconstriction/dilation. If the user has indicated that they have taken a particular type of medication, which is known to have a known side effect which affects vasoconstriction/dilation, then at step S108 the optimal air output is adjusted to take this into account. In particular as the medication may cause a temporary increase, or decrease, in the body temperature of the user, which is due to a physiological response to the medication and not motion sickness. As such the optimal air output is adjusted to take into account variation in body temperature due to the medication.

In further examples, dietary information, such as that logged in a lifestyle app, is used at step S108 when determining the optimal air output. The consumption of food is known to change heart rate, in particular the resting heart rate. For example, an occupant who is on a calorie controlled diet, will have a different heart rate baseline that someone who is at a constant weight, and a different heart rate than someone experiencing weight gain. As such, the increase in heart rate associated with food consumption would be measurable by the sensors but not attributed to motion sickness. Thus the optimal air output is adjusted accordingly.

Thus the collected and measured physiological data, motion data, and optional lifestyle data is used to vary the HVAC.

Steps S102 to S108 may be repeated over time to provide vary the target ambient temperature and flow in accordance with the occupant's reaction to the optimal flow of air from the HVAC.

In further embodiments if the occupant's activity is tracked via a calendar, or fitness app, such information is used at step S108 to determine the optimal temperature. If it is known that the occupant is likely to have a higher body temperature due to exercise, and the physiological data shows an increased heat flow rate then the target ambient temperature may be lowered to account for the exercise. In particular the target ambient temperature may be lowered for a first period of time whilst the user cools down and a second target ambient (possibly higher) temperature is calculated for when the occupant has initially cooled down.

In further embodiments historic data is used to determine the optimal air output and temperature settings for the HVAC.

At step S110 the determined air output values (temperature and flow rate) are sent to a controller of the HVAC or vehicle climate control unit and the system outputs air at the determined value thereby providing an optimal level of occupant comfort.

As such the process ensures that the air output setting, including temperature and air flow is optimised to ensure occupant comfort.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

The invention claimed is:

1. A wearable electronic device comprising: a communication unit configured to communicate with external devices; a heat flow sensor configured to measure a rate of heat energy flowing through a user's skin; a processor configured to calculate a target ambient temperature for the user based on the measured heat flow through the user's skin; wherein the communication unit is configured to transmit a signal to a vehicle climate system, the signal indicative of the calculated target ambient temperature, wherein the signal is configured to cause the vehicle climate system to provide the target ambient temperature; and a memory configured to store a plurality of measured values of heat flow through the user's skin over time; wherein the processor is further configured to: determine, based on the plurality of measured values of heat flow through the user's skin over time, a baseline heat flow value; and calculate the target ambient temperature for the user based on the determined baseline heat flow value.

2. The wearable electronic device of claim 1, wherein the heat flow sensor is a heat flux sensor.

3. The wearable electronic device of claim 1, wherein the processor is further configured to: determine, based on the plurality of measured values of heat flow, a deviation in heat flow through the user's skin from the baseline heat flow value; and calculate the target ambient temperature for the user based on the determined deviation in heat flow through the user's skin from the baseline heat flow value.

4. The wearable electronic device of claim 1, wherein: the memory is further configured to store calendar data; and the processor is further configured to: determine, based on the calendar data, a first time period during which the heat flow through the user's skin is expected to deviate from the baseline heat flow value; and calculate either or both of: a first target ambient temperature for the user for the first time period; and a second target ambient temperature for the user for a second time period that is subsequent to the first time period.

5. The wearable electronic device of claim 1, further comprising at least one additional sensor selected from a group consisting of: a temperature sensor; a heart rate sensor; and a heart rate variability sensor; wherein the processor is configured to calculate the target ambient temperature for the user based on the measured heat flow through the user's skin and at least one further measurement taken by the at least one additional sensor.

6. A system comprising the wearable electronic device of claim 1 and a controller for operating a vehicle climate system.

7. A vehicle comprising the system of claim 6.

* * * * *